(12) United States Patent
Alty et al.

(10) Patent No.: US 7,482,499 B2
(45) Date of Patent: Jan. 27, 2009

(54) FLUOROBUTENE DERIVATIVES AND PROCESS FOR PRODUCING SAME

(75) Inventors: Adam C. Alty, Alachua, FL (US); Richard A. Du Boisson, Alachua, FL (US)

(73) Assignee: Central Glass Company, Limited, Ube-shi (JP)

( * ) Notice: Subject to any disclaimer, the term of this patent is extended or adjusted under 35 U.S.C. 154(b) by 279 days.

(21) Appl. No.: 10/554,783

(22) PCT Filed: Apr. 28, 2004

(86) PCT No.: PCT/US2004/013029

§ 371 (c)(1), (2), (4) Date: Oct. 28, 2005

(87) PCT Pub. No.: WO2004/096737

PCT Pub. Date: Nov. 11, 2004

(65) Prior Publication Data

US 2006/0205986 A1    Sep. 14, 2006

(51) Int. Cl.
*C07C 17/00*   (2006.01)
(52) U.S. Cl. ................................ 570/156; 570/155
(58) Field of Classification Search .......... 570/156, 570/175, 155
See application file for complete search history.

(56) References Cited

U.S. PATENT DOCUMENTS 2,442,993 A * 6/1948 Cass .................... 570/155
2,461,523 A * 2/1949 Coffman et al. ........... 570/156
2,599,631 A   6/1952 Harmon et al.
2,750,431 A   6/1956 Tarrant et al.
5,986,151 A * 11/1999 Van Der Puy ............. 570/175

FOREIGN PATENT DOCUMENTS

WO    WO 2004/058827 A1    7/2004

OTHER PUBLICATIONS

European Search Report dated Aug. 31, 2006 (Three (3) pages).

* cited by examiner

*Primary Examiner*—Jafar Parsa
(74) *Attorney, Agent, or Firm*—Crowell & Morning LLP

(57) ABSTRACT

The present invention provides novel compounds, 2,4,4,4-tetrafluoro-1-butene and (E)- and (Z)-1,1,1,3-tetrafluoro-2 butenes. Furthermore, the present invention provides the following novel first and second processes for producing 2,4,4,4-tetrafluoro-1-butene, (E)- and (Z)-1,1,1,3-tetrafluoro-2-butenes, and 1,1,3-trifluorobutadiene. The first process is a process for producing 2,4,4,4-tetrafluoro-1-butene by heating 1,1,1,3,3-pentafluorobutane at from about 200° C. to about 700° C. The second process is a process for producing (E)- and (Z)-1,1,1,3-tetrafluoro-2-butenes by bringing 1,1,1,3,3-pentaflurobutane with a base. By the first and second processes, it is possible to obtain respective target fluorobutenes with high selectivity. In third to fifth processes, 2,4,4,4-tetrafluoro-1-butene, (E)- and (Z)-1,1,1,3-tetrafluoro-2-butene, and 1,1,3,-trifluorobutadiene can be produced by heating 1,1,1,3,3-pentafluorobutane in the presence of a catalyst. This catalyst can be regenerated by the contact with a halogen-containing gas in sixth process.

16 Claims, No Drawings

FLUOROBUTENE DERIVATIVES AND PROCESS FOR PRODUCING SAME

CROSS REFERENCE TO RELATED DOCUMENTS

This specification contains subject matter in common with Disclosure Document No. 492915 entitled "Thermal Dehydrofluorination of HFC's" submitted by Adam C. Alty and Richard A. Du Boisson to the United States Patent and Trademark Office on May 1, 2001, and hereby claims all benefits legally available from said disclosure document. In addition, the contents of said disclosure documents are incorporated herein by reference.

BACKGROUND OF THE INVENTION

The present invention relates to novel fluorobutenes. Furthermore, it relates to a process for producing fluorobutenes and a fluorobutadiene by a dehydrofluorination with a raw material of a polyfluorobutane.

Fluorobutenes and fluorobutadienes are useful as monomers for fluorine-containing polymers, synthesized intermediates/building blocks for producing fluorine-containing intermediates, and raw materials for producing hydrofluorocarbons.

Thermal dehydrofluorination is a well-known process for synthesizing olefins. Dehydrochlorination is widely used for forming a carbon-carbon multiple bond. Furthermore, there are several examples of thermal dehydrochlorination process used for producing fluoroolefins. On the other hand, almost all of thermal dehydrofluorinations are impractical based on a general knowledge due to their low conversion and low selectivity.

As its theoretical background, there is provided that the energy necessary for severing a C—F bond is close to that necessary for severing a carbon-carbon bond since the carbon-fluorine bond is very strong. In general, the temperature necessary for releasing hydrogen fluoride (HF) is far higher than the temperature for dehydrochlorination of an analogous substance containing chlorine atom instead at the defluorination site. Under a high temperature condition necessary for conducting the dehydrofluorination, molecular decomposition reactions and rearrangement reactions compete, thereby lowering selectivity. U.S. Pat. No. 2,480,560 describes that non-catalytic dehydrofluorinations of five different hydrofluorocarbons give fluoroolefins with low selectivity.

Even in the examination process in relation to the present invention of the present inventors, when 1,1,1,4,4,4-hexafluorobutane (HFC-356mfc) had been added to a nickel reaction tube at 630° C., it mainly gave trifluoromethane and 3,3,3-trifluoropropene with a conversion of 56%, and it was not possible to obtain 1,1,4,4,4-pentafluoro-1-butene, which is considered to be formed by dehydrofluorination (Comparative Example 1). Furthermore, when 2-trifluoromethyl-1,1,1-trifluoropropane was similarly treated at 660° C., it mainly gave trifluoromethane and 3,3,3-trifluoropropene, and it was not possible to obtain 2-trifluoromethyl-1,1-difluoropropene, which is considered to be formed by dehydrofluorination (Comparative Example 2).

In order to overcome such problems and to efficiently produce fluoroolefins, much effort has been made in the development of catalytic dehydrofluorination. By catalytic process, it may be possible that hydrogen fluoride is released at a temperature lower than that at which the above side reactions become noticeable, thereby causing an expectation for improving selectivity. U.S. Pat. No. 2,599,631 describes both of thermal (non-catalytic) and catalytic processes for producing vinyl fluoride by dehydrofluorination of 1,1-difluoroethane and shows that the catalytic process is more useful. However, one of large problems of the catalytic dehydrofluorination process is a rapid deactivation of the catalyst due to by-products and polymerization products.

Another means for producing fluoroolefins by dehydrofluorination is a process by contact with a base. However, in general, a base-used dehydrofluorination gives in many cases isomers that are different from products obtained by a thermal dehydrofluorination process, and therefore it has been difficult to say that it is an efficient production process of necessary fluoroolefins.

SUMMARY OF THE INVENTION

It is an object of the present invention to provide 2,4,4,4-tetrafluoro-1-butene and (E)- and (Z)-1,1,1,3-tetrafluoro-2-butenes, which are novel fluoroolefins. It is another object of the present invention to provide an industrially achievable process for producing these compounds and their derivative, 1,1,3-trifluorobutadiene (1,1,3-Trifluoro-buta-1,3-diene).

In order to solve the above problems, the inventors have eagerly conducted an examination on reaction systems applicable to thermal (non-catalytic) dehydrofluorinations. As a result, it was surprisingly found that 1,1,1,3,3-pentafluorobutane gives 2,4,4,4-tetrafluoro-1-butene, which is a novel fluorine-containing compound and becomes a raw material for useful fluorine-containing synthesis intermediates, highly selectively with high conversion by a thermal, non-catalytic dehydrofluorination. It was also found that conversion and selectivity of the reaction particularly improve under a specific condition such as passing through a heated reaction tube ("a first process").

The present inventors further found that (E)- and (Z)-1,1,1,3-tetrafluoro-2-butenes, which are novel compounds, are given by heating 1,1,1,3,3-pentafluorobutane and that selectivity of (E)- and (Z)-1,1,1,3-tetrafluoro-2-butenes particularly improves by bringing 1,1,1,3,3-pentafluorobutane with a base ("a second process").

As a result of a further study, the present inventors have found that a dehydrofluorination, corresponding to the first process, occurs by heating 1,1,1,3,3-pentafluorobutane in the presence of a particular catalyst under a condition that is milder than that of the first process, thereby providing 2,4,4,4-tetrafluoro-1-butene with high yield ("a third process"). It was found that the discovered catalyst is long in catalyst lifetime and is sufficiently endurable for a large-scale industrial use and that it is a particularly preferable process for producing 2,4,4,4-tetrafluoro-1-butene. Together with this reaction, it was found that (E)- and (Z)-1,1,1,3-tetrafluoro-2-butenes are obtained ("a fourth process") and that 1,1,3-trifluorobutadiene, which is useful as a synthesis intermediate or the like, is also obtained ("a fifth process"). In general, respective compounds are generated simultaneously in the system. However, it was confirmed that each component can be isolated by conducting a purification process (such as distillation) after the reaction.

Although the above-mentioned each catalytic dehydrofluorination proceeds competitively by heating 1,1,1,3,3-pentafluorobutane in the presence of a catalyst, selectivity of the target compound may vary depending on the type of catalyst and the reaction temperature. In other words, depending on which product is selected as the target compound, preferable catalysts and reaction temperature may vary. Hereinafter, the case where 2,4,4,4-tetrafluoro-1-butene is selected as the target product refers to the third process, the case where (E)- and (Z)-1,1,1,3-tetrafluoro-2-butenes are selected as the target products refers to the fourth process, and the case where 1,1,3-trifluorobutadiene is selected as the target product refers to the fifth process.

The present inventors have eagerly conducted a further study on the above catalytic dehydrofluorinations. As a result, we found that it is possible to effectively regenerate the catalyst (a sixth process) by treating the catalyst with a halogen-containing gas (e.g., hydrogen fluoride, hydrogen chloride, and chlorine) during or after the reaction of the third, fourth or fifth process.

That is, the present invention provides 2,4,4,4-tetrafluoro-1-butene and (E)- and (Z)-1,1,1,3-tetrafluoro-2-butenes, which are useful novel compounds as fluorine-containing intermediates, using low-price 1,1,1,3,3-pentafluorobutane as the raw material and using a thermal (non-catalytic) dehydrofluorination, a catalytic dehydrofluorination, or a base-contact dehydrofluorination. Furthermore, the present invention provides processes for producing these 2,4,4,4-tetrafluoro-1-butene and (E)- and (Z)-1,1,1,3-tetrafluoro-2-butenes and 1,1,3-trifluorobutadiene, which can be conducted in an industrial scale.

The first and third processes and the second and fourth processes of the present invention are respectively summarized as the following formulas 1 and 2.

Formula 1 (the first and third processes):

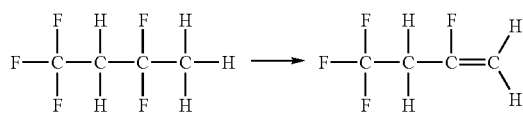

Formula 2 (the second and fourth processes):

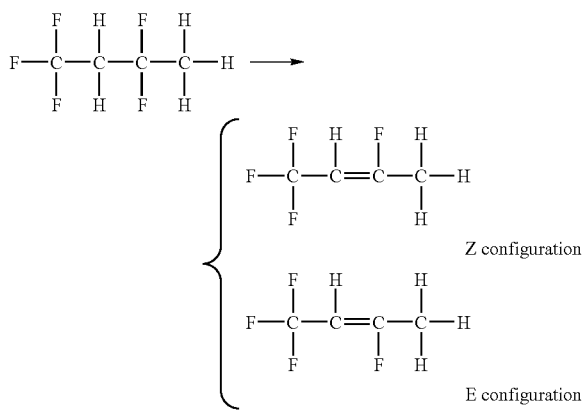

The fifth process of the present invention is summarized as the following formula 3.

Formula 3 (the fifth process):

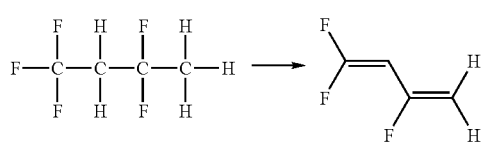

DESCRIPTION OF THE PREFERRED EMBODIMENTS

In the following, the present invention is explained in detail. Firstly, the first process of the present invention, a production of 2,4,4,4-tetrafluoro-1-butene by a thermal, non-catalytic dehydrofluorination of 1,1,1,3,3-pentafluorobutane, is described. This butene is a novel substance, its production has not been described up to now, and it is a synthesis raw material of fluorine-containing intermediates useful in the fields of medicines and agricultural chemicals.

This first process is achieved by heating 1,1,1,3,3-pentafluorobutane, which is industrially available as 365mfc, at from about 200° C. to about 700° C. As to the temperature of this dehydrofluorination, it can generally be conducted in a range of about 200° C. to about 700° C., preferably 300° C.-600° C. It is effective to maintain the reaction temperature in a range of 400° C.-550° C. in order to obtain the optimum conversion and selectivity.

It is preferable to conduct the first process under a substantially base-free condition (i.e., under an acid or neutral condition). Herein, "base" refers to a substance known as a basic substance. For example, a compound showing a pH of 8 or higher, when dissolved in water to a have a concentration of 0.1 mol dm$^{-3}$, corresponds thereto. Even when the reaction is conducted under a condition under which such base is not coexistent, the cleavage of a carbon-carbon bond is prevented, and it is possible to obtain 2,4,4,4-tetrafluoro-1-butene with high selectivity.

The reaction manner of the first process is either flow (continuous) type or batch type. In many cases, it is possible in the reaction to obtain a preferable selectivity by subjecting 1,1,1,3,3-pentafluorobutane to a high-temperature treatment for a relatively short time. Therefore, flow type is more preferable. It becomes necessary in general to have pressurization in the reaction of batch type. In contrast, the reaction of flow type proceeds sufficiently under normal pressure. Therefore, flow type is advantageous from the viewpoint of operability.

In the case of batch type, there is considered a process in which 1,1,1,3,3-pentafluorobutane is introduced into a reactor that is resistant against the pressurization condition and against the contact with hydrogen fluoride, followed by sealing and heating with stirring. Upon this, it is desirable that the inside sample is occasionally sampled, that the analysis is conducted by a method such as gas chromatography, and that the reaction step is terminated at the time when the raw material has sufficiently been consumed and converted into the product.

In contrast with this, the flow-type reaction is achieved by heating and vaporizing 1,1,1,3,3-pentafluorobutane and by allowing it to flow through a thermal reaction tube. The thermal reaction tube must be constructed from a material that is resistant against the contact with hydrogen fluoride even at high reaction temperature. In some cases, this is filled with a filler that has resistance against hydrogen fluoride, in order to improve the mixing effect and the thermal contact, and that is preferable in general. For example, although it is possible to use a nickel alloy for the reaction tube and Monel Pro-pack for the filler, it is not limited to this.

In the following, in the present specification the term "raw material input standard contact time" is defined as follows. That is, "the value obtained by subtracting the solid phase volume occupied by the filler from the inside volume of the reaction tube" is referred to as "column volume", and in the following it is represented by A, too. On the other hand, "the volume of the raw material gas introduced into the reaction tube per second" is represented by B. The value of B is calculated from mol number of the raw material introduced per second, from pressure and from temperature, assuming that the raw material gas is ideal gas. Upon this, the value (=A/B) obtained by dividing A by B is referred to as "raw material input standard contact time". In the reaction tube, HF and other gases are produced as by-products, and the mole number change occurs. However, these are not taken into consideration upon calculating "contact time". The contact time of the reaction gas in ideal condition in which selectivity of the dehydrofluorination is 100% with 100% conversion becomes a half of the raw material input standard contact time herein referred to.

The thus calculated "raw material input standard contact time" is not particularly limited. In the case of maintaining the reaction temperature in a range of 400° C.-550° C. as mentioned above, from about 60 column volume to 300 column volume per hour (about 12 seconds to 60 seconds in raw material input contact time) is preferable. The introduction with from about 90 column volume to about 200 column volume per hour (about 18 seconds to 40 seconds in raw material input contact time) is more preferable. On the other hand, when the raw material input contact time exceeds 200 seconds, side reactions tend to occur. When the raw material input contact time is less than 1 second, conversion is low. Therefore, it is not preferable.

From the above, under a base-free condition, the passing of 1,1,1,3,3-pentafluorobutane through a reaction tube heated at 400° C.-550° C. with an input raw material contact time of from 18 second to 40 seconds is a particularly preferable embodiment in the first process of the present invention.

The optimum contact time depends on the temperature (reaction temperature), shape and filler of the reaction tube. Therefore, it is desirable to set the optimum value by suitably adjusting the raw material supply rate (raw material input contact time) for each set temperature, each reaction tube shape and each filler type. In conducting the present invention, a person skilled in the art is not prevented from such optimization. In general, the adoption of a contact time capable of obtaining a raw material conversion of 25% or higher is preferable from the viewpoint of the recovery and the reuse of the unreacted raw material. More preferably, it is adjusted so that the conversion becomes 70% or more.

Although the reaction pressure may be lower or higher than the atmospheric pressure or under atmosphere, under the atmospheric pressure is generally preferable. It is also possible to conduct the reaction in the presence of an inert gas (such as nitrogen and argon) that is stable under the reaction conditions or in the presence of an excessive HF.

The dehydrofluorination process of this invention can be conducted in a gas phase using a well-known chemical engineering apparatus. The reaction tube, a related raw-material introduction system, an outflow system and a related unit are made of a material strong against hydrogen fluoride. As typical materials, particularly stainless steel material such as austenite-type, or high nickel alloy and copper clad steel such as Monel nickel-copper alloy, Hastelloy nickel alloy and Inconel nickel-chromium alloy can be exemplified. However, it is not limited to this.

In a reaction mixture obtained by the first process, 1,1,1,3, 3-pentafluorobutane (the raw material) and (E)- and (Z)-1,1, 1,3-tetrafluoro-2-butenes (by-products) are coexistent with the target product, 2,4,4,4-tetrafluoro-1-butene. However, the present inventors found that these compounds have boiling points sufficiently different from each other and do not cause azeotropic phenomena (2,4,4,4-tetrafluoro-1-butene boiling point: 29-30° C., 1,1,1,3,3-pentafluorobutane boiling point: 40° C., (E)-1,1,1,3-tetrafluoro-2-butene: 18-19° C., and (Z)-1,1,1,3-tetrafluoro-2-butene: 48-49° C. Each is the boiling point at atmospheric pressure.)

Therefore, it is possible to isolate the target 2,4,4,4-tetrafluoro-1-butene with high purity by obtaining a reaction mixture by the first process and then by subjecting this reaction mixture to distillation. Although there are no particular limitations on the conditions of this distillation, it is the simplest to conduct that at normal pressure. According to the present invention, it is possible to easily isolate the target 2,4,4,4-tetrafluoro-1-butene without conducting a complicated purification operation after the reaction. Therefore, it is particularly advantageous in producing 2,4,4,4-tetrafluoro-1-butene industrially.

Furthermore, after recovery of the unreacted starting material (1,1,1,3,3-pentafluorobutane), its reuse becomes possible by introducing it again into the reactor.

Next, the second process of the present invention, a process for highly selectively providing (E)- and (Z)-1,1,1,3-tetrafluoro-2-butenes by dehydrofluorinating 1,1,1,3,3-pentafluorobutane, is described in detail.

As mentioned in the first process, it is possible to obtain (E)- and (Z)-1,1,1,3-tetrafluoro-2-butenes together with 2,4, 4,4-tetrafluoro-1-butene (a main product) by subjecting 1,1, 1,3,3-pentafluorobutane to a heating treatment at from about 200° C. to about 700° C.

However, the inventors found that it is particularly effective to bring 1,1,1,3,3-pentafluorobutane into contact with a base to dehydrofluorinate it, thereby obtaining (E)- and (Z)-1,1,1, 3-tetrafluoro-2-butenes with higher selectivity and yield.

Hereinafter, a dehydrofluorination of 1,1,1,3,3-pentafluorobutane using a base is described in detail. (E)- and (Z)-1,1, 1,3-tetrafluoro-2-butenes are novel compounds, and there have been no synthesis reports in the past. These are isomers of 1-butene obtained from the above-described thermal dehydrofluorination. The above-mentioned thermal dehydrofluorination of 1,1,1,3,3-pentafluorobutane (the first process) and a dehydrofluorination of 1,1,1,3,3-pentafluorobutane by a base (the second process) are complementary, and it becomes possible to produce useful, different positional isomers of tetrafluorobutene.

Although there are no particular limitations on the base to be used, it is possible to cite alkali metal hydroxides (potassium hydroxide, sodium hydroxide, lithium hydroxide and the like), alkali metal carbonates (sodium carbonate, potassium carbonate, sodium hydrogencarbonate, potassium hydrogencarbonate and the like), alkali earth metal hydroxides (calcium hydroxide, magnesium hydroxide and the like), organic bases (tertiary amines such as triethylamine, tributylamine, and trimethylamine; primary amines such as monoethylamine, monobutylamine, cyclohexylamine, and aniline; secondary amines such as diethylamine and dibutylamine; aromatic bases such as pyridine, picoline, lutidine, and ethylpyridine; and strong bases such as guanidine and 1,8-diazabicyclo[5.4.0]dec-7-ene (DBU)) or other strong bases (such as sodium methoxide, sodium ethoxide, potassium methoxide, and potassium ethoxide) that are commonly used in analogous reactions. Of these, potassium hydroxide, sodium hydroxide and calcium hydroxide and the like of low prices are particularly preferable.

Although the reaction is achieved by bringing the raw material 1,1,1,3,3-pentafluorobutane with a base, it is desirable to gradually mix both in order to maintain the reaction conditions mildly. For example, it is possible to cite a process such as a gradual addition of the raw material 1,1,1,3,3-pentafluorobutane with stirring of a base-containing liquid. On the contrary, it is also possible to allow the reaction to proceed by adding a base to the raw material 1,1,1,3,3-pentafluorobutane. The base can be used as an aqueous solution or a simple substance, and it is possible to add a phase transfer catalyst. For example, since 85% potassium hydroxide melts by heating to 100° C. or higher, it is convenient that this liquid in the melted condition is stirred and the raw material 1,1,1,3,3-pentafluorobutane is added dropwise thereto.

The base may be used as a solution by dissolving it in a solvent. As the solvent of this case, there may be used water, ethers (e.g., diethyl ether, dibutyl ether, methyl butyl ether, phenetole, dioxane, tetrahydrofuran, tetrahydropyran, anisole, benzyl ether, glymes (e.g., monoglyme, diglyme, and triglyme)) and halogen-containing solvents (e.g., methylene chloride, 1,1-dichloroethane, 1,2-dichloroethane, chloroform, carbon tetrachloride, chlorobenzene, 1,4-bis(trifluoromethyl)benzene) and the like. In other cases, it may be preferable to use in the reaction a commonly-used phase-transfer catalyst (e.g., 18-crown-6, dibenzo-18-crown-6, dicyclohexano-18-crown-6, 12-crown-4,15-crown-5, dibenzo-24-crown-8, tetraethylammonium chloride, tetraethylammonium bromide, tetrabutylammonium chloride, tetrabutylammonium bromide, ethyltributylammonium bromide, tetraphenylammonium bromide, and tetraphenylphosphonium bromide).

Although there are no particular limitations on the reaction temperature of the process for producing (E)- and (Z)-1,1,1,3-tetrafluoro-2-butenes by the contact with this base, from 0° C. to 300° C. is preferable, and more preferably it is a range of from 30° C. to 250° C.

The reaction pressure may be lower or higher than atmospheric pressure. In general, the vicinity of atmospheric pressure is simple and preferable.

Although there are no particular limitations on the reaction time, the reaction is fast under a heated condition, and the reaction occurs immediately when the raw material and a base are mixed together. Therefore, as shown in the after-mentioned Example 2, a process is simple, in which mixing of the raw material and a base is conducted under an open condition (atmospheric pressure), and a mixed gas of the raw material and the product is cooled down, thereby collecting it as a liquid (reaction mixture).

However, it is not limited to such process. A dehydrofluorination process of the second process can be conducted by a batch manner or in a continuous reaction apparatus using a known chemical engineering technique. The apparatus and its related raw material introducing line, the outflow line, and related units should be made from a material that is resistant against strong bases. Typical examples of the material are stainless steel, carbon steel, or high nickel alloys such as Monel-nickel copper alloy, Hastelloy-nickel alloy and Inconel nickel-chromium alloy, and copper clad steel. In limited cases, it is possible to use glass or glass-lined steel.

Similar to the first process, it is also possible to separate each component from the reaction mixture obtained by this second process by a distillation operation. Specifically, it is possible to isolate the unreacted 1,1,1,3,3-pentafluorobutane (boiling point=40° C.), (E)-1,1,1,3-tetrafluoro-2-butene (boiling point=18-19° C.), and (Z)-1,1,1,3-tetrafluoro-2-butene (boiling point=48-49° C.) as each distillate. Although there are no particular limitations on this distillation condition, it is the simplest to conduct it at normal pressure. Since by-products generated by the present reaction are low-boiling-point compounds such as butadiene and butyne, it is easy to separate these. Since it is possible to easily obtain (E)- and (Z)-1,1,1,3-tetrafluoro-2-butenes of high purity, it is possible to obtain a high purity diastereomer by apply a diastereoselective reaction. Therefore, it is highly useful as a synthesis raw material.

The recovered raw material 1,1,1,3,3-pentafluorobutane can be reused as a reaction raw material of the first process or second process.

Next, the processes (i.e., the third, fourth and fifth processes of the present invention) for producing 2,4,4,4-tetrafluoro-1-butene, (E)- and (Z)-1,1,1,3-tetrafluoro-2-butenes, and 1,1,3-trifluorobutadiene are explained. Firstly, features common to the third, fourth and fifth processes are described.

In contrast with the first process, each of the third, fourth and fifth processes is characterized in that catalyst is used. Such catalyst may be (a) an active metal species, (b) a material (hereinafter may be referred to as "catalyst carrier) that is commonly known as a catalyst carrier and has a large specific surface area, or (c) a carried catalyst having the active metal species carried on the catalyst carrier. Since these catalysts (a), (b) and (c) serve to lower the activation energy, it is possible to obtain each target compound at a reaction temperature that is significantly lower than that of the first process. Furthermore, as in the fifth process, it is possible to obtain 1,1,3-trifluorobutadiene, which can hardly be obtained in the first and second processes.

Examples of (a) the active metal species include titanium, chromium, manganese, iron, cobalt, nickel, copper, zirconium, niobium, molybdenum, ruthenium, rhodium, palladium, silver, hafnium, tantalum, tungsten, rhenium, iridium, platinum, and antimony. In particular, preferable examples are titanium, chromium, manganese, iron, cobalt, nickel, zirconium, niobium, molybdenum, tantalum, and tungsten.

Preferable examples of (b) the catalyst carrier include activated carbons, which are produced by heat treatment of vegetable components (e.g., coconut husk) and high-boiling-point components of petroleum, and oxides (e.g., alumina, titania, niobia, and zirconia). Of these, coconut husk activated carbon, which is large in specific surface area, is particularly preferable. In particular, a catalyst having a specific surface area of 500-2,000 $m^2$/g is preferable.

Each of (a) the active metal species and (b) the catalyst carrier can be used alone, since each of them has a catalytic activity. However, an active metal species of a high catalyst activity acts under a large specific surface area condition by using (c) the carried catalyst, which is obtained by combining the catalysts (a) and (b) together. Therefore, the use of (c) the carried catalyst is particularly advantageous for the reaction and allows the reaction to proceed under a milder condition. Thus, it is particularly preferable to use (c) the carried catalyst for conducting the third to fifth processes. Preferable examples of (c) the carried catalyst contain active metal species (i.e. titanium, chromium, manganese, iron, cobalt, nickel, zirconium, niobium, molybdenum, tantalum, and tungsten) each carried on activated carbon carrier. Of these, particularly preferable examples are Cr/C (representing chromium atoms carried on activated carbon), Ti/C, Fe/C, Ni/C, Nb/C and Ta/C.

In the case of using (c) the carried catalyst, the amount of the active metal species (in terms of the weight of metal atoms) is preferably from 1 g to 20 g, relative to 100 g of the activated carbon carrying the active metal species. With this, it is possible to have a high catalytic activity and makes the reaction economical. If it is less than 1 g, yield may become too low. If it is greater than 20 g, the cost for producing the catalyst may become too high. This makes the reaction uneconomical. The carried catalyst may be a commercial product.

In order to obtain a high-activity and long-lifetime catalyst, it is particularly effective to previously conduct a treatment of bringing a flow of halogenated hydrogen gas (e.g., hydrochloric acid and hydrofluoric acid) into contact with the catalyst. It is preferable to conduct this treatment by gradually increasing the treatment temperature from about 50° C. to a temperature that is higher than the reaction temperature by about 50° C. In particular, heat of adsorption is generated immediately after the treatment. Therefore, it is preferable to conduct the treatment, while the halogenated hydrogen gas is diluted with an inert gas (e.g., nitrogen). Although the treatment time is not particularly limited, it is preferably from 3 hr to 24 hr.

Although the dehydrofluorinations of the third to fifth processes may usually proceed in parallel, selectivity of the product may vary depending on the type of the catalyst, as described hereinafter.

Although each of the third to fifth processes may be conducted in a continuous manner or batch-wise, the continuous manner is preferable since it is superior in operability and since the sixth process can be conducted by using the same reaction tube without necessity of taking the catalyst out of the reaction tube.

In the case of the batch-wise operation, each process may be conducted by introducing 1,1,1,3,3-pentafluorobutane into a reactor made of a material that is pressure-proof and is resistant against hydrogen fluoride, following by sealing, stirring and heating. In each process, it is preferable to terminate the reaction after confirming that the raw material was sufficiently consumed, by checking the progress of the reaction by a suitable analytical technique (e.g., gas chromatography).

In contrast, the continuous operation is conducted by heating 1,1,1,3,3-pentafluorobutane to gasify the same and then by allowing it to flow through a reaction tube charged with a catalyst. The continuous operation can be conducted by using a fixed bed or fluidized bed. The reaction tube is preferably made of a material that is resistant against the contact with hydrogen fluoride even at high reaction temperature. The dehydrofluorination of the present invention can be conducted in a gas phase by using a known chemical engineering apparatus. It is preferable that each of the reaction tube, a related system for introducing the raw material, a system for allowing the product to flow out, and a related unit is made of a material that is resistant against hydrogen fluoride. Non-limitative examples of this material are stainless steel materials (e.g., austenite) and high nickel alloys and copper cladding steels (e.g., Monel nickel-copper alloy, Hastelloy nickel alloy, Inconel nickel-chromium alloy).

In the case of the continuous operation, the above-defined raw material input standard contact time, during which the gasified 1,1,1,3,3-pentafluorobutane is brought into contact with the catalyst of the reaction tube, is preferably from 2 seconds to 120 seconds, more preferably from 5 seconds to 45 seconds. If it is shorter than 1 second, conversion may become too low, thereby lowering the productivity. Furthermore, the load on the catalyst may become too much, thereby accelerating deterioration of the catalyst. If it is longer than 120 seconds, the productivity per unit time per reactor may become too low.

Although the reaction pressure may be lower or higher than or under atmospheric pressure, it is preferable to conduct the reaction under atmospheric pressure due to operation easiness and smooth progress of the reaction. Furthermore, the reaction may be conducted in the presence of an inert gas (e.g., nitrogen and argon) that is stable under the reaction condition or in the presence of excessive HF.

As compared with the first process with no use of catalyst, it is possible to conduct the reactions of the third to fifth processes under milder conditions (i.e., under lower temperature) to obtain the target products with high yield. The reaction temperatures of the third to fifth processes may be 150° C. to 700° C., preferably 150° C. to 500° C. to take advantage of a milder reaction condition than that of the first process. As described hereinafter, selectivity of each target compound depends on the reaction temperature. Furthermore, the optimum reaction temperature may vary depending on the catalyst type. Therefore, a preferable reaction temperature of the third to fifth processes may vary depending on the target compound and the catalyst used.

As mentioned above, each reaction product of the third to fifth processes is usually in the form of a mixture. This mixture can be separated into pure components by conducting a purification operation (e.g., distillation) after the reaction, since major components have different boiling points (i.e., the unreacted 1,1,1,3,3-pentafluorobutane: 40° C.; 2,4,4,4-tetrafluoro-1-butene: 29-30° C.; (E)-1,1,1,3-tetrafluoro-2-butene: 18-19° C.; (Z)-1,1,1,3-tetrafluoro-2-butene: 48-49° C.; and 1,1,3-trifluorobutadiene: 16° C.). To conduct distillation under normal pressure (e.g., atmospheric pressure) is simple and thus preferable.

Similar to the first and second processes, it is possible to recover the unreacted 1,1,1,3,3-pentafluorobutane (365mfc) and reuse it in the subsequent reaction in the third to fifth processes.

In the following, each feature specific to the third, fourth or fifth process is described in detail.

In the third process for producing 2,4,4,4-tetrafluoro-1-butene as the target compound, particular preferable catalysts include activated carbon alone, Cr/C, and Ti/C. In the case of using activated carbon alone as the catalyst, the reaction temperature is preferably 300° C. to 500° C., more preferably 350° C. to 450° C., since the generation of the target compound may start as the reaction temperature reaches the vicinity of 300° C. In the case of using Cr/C or Ti/C as the carried catalyst, the reaction temperature is preferably 150° C. to 400° C., more preferably 200° C. to 350° C., since the generation of the target compound may start as the reaction temperature reaches the vicinity of 150° C. The generation of the target product is found even at a temperature higher than the above preferable ranges. This is, however, not preferable in terms of energy efficiency and preventing the apparatus from having a corrosion by HF as a by-product. It is particularly preferable to conduct the third process at a temperature in the vicinity of 250° C. (i.e., from 200° C. to 300° C.) in the presence of Ti/C catalyst since both conversion and selectivity can be particularly high.

In the fourth process for producing (E)-1,1,1,3-tetrafluoro-2-butene or (Z)-1,1,1,3-tetrafluoro-2-butene as the target compound, particular preferable catalysts include activated carbon alone and Cr/C. In the case of using activated carbon alone as the catalyst, the reaction temperature is preferably 300° C. to 500° C., more preferably 350° C. to 450° C., since the generation of the target compound may start as the reaction temperature reaches the vicinity of 300° C. In the case of using Cr/C as the carried catalyst, the reaction temperature is preferably 150° C. to 350° C., more preferably 200° C. to 300° C., since the generation of the target compound may start as the reaction temperature reaches the vicinity of 150° C. The generation of the target product is found even at a temperature higher than the above preferable ranges. This is, however, not preferable in terms of energy efficiency and preventing the apparatus from having a corrosion by HF as a by-product. It is particularly preferable to conduct the fourth process at a temperature in the vicinity of 250° C. (i.e., from 200° C. to 300° C.) in the presence of Cr/C catalyst since both conversion and selectivity can be particularly high.

In the fifth process for producing 1,1,3-trifluorobutadiene as the target compound, particular preferable catalysts include activated carbon alone and Cr/C. It is preferable to conduct the fifth process at a temperature that is somewhat higher than that of the fourth process in order to improve selectivity of the target compound. In the case of using activated carbon alone as the catalyst, the reaction temperature is preferably 350° C. to 600° C., more preferably 400° C. to 500° C., since it is possible to find a significant generation of the target compound at a reaction temperature of 350° C. or higher.

In the case of using Cr/C in the fifth process, the reaction temperature is preferably 250° C. to 500° C., more preferably 300° C. to 500° C., still more preferably 300° C. to 450° C., since a significant generation of the target compound may start as the reaction temperature reaches 250° C. The generation of the target product is found even at a temperature higher than the above preferable ranges. This is, however, not preferable in terms of energy efficiency and preventing the apparatus from having a corrosion by HF as a by-product.

In the third to fifth processes, the recovered 1,1,1,3,3-pentafluorobutane (the unreacted raw material) can be reused as the raw material for conducting the first to fifth processes. It is possible to reuse the reaction product (a mixture containing 1,1,1,3,3-pentafluorobutane) of the third, fourth or fifth process, as the raw material for conducting the fifth process to obtain 1,1,3-trifluorobutadiene.

Although the catalyst to be used in the third, fourth or fifth process is high in durability, it can be regenerated by the sixth process when its activity becomes low by a long-term use. In fact, it is possible in the six process to regenerate the catalyst by charging an apparatus (e.g., reaction tube) similar to that of the continuous operation of the first to fifth processes, with a deteriorated catalyst, and then by allowing a halogenated hydrogen gas (e.g., hydrochloric acid (hydrogen chloride gas) and hydrofluoric acid (hydrogen fluoride gas)) or halogen gas (e.g., chlorine), in place of 1,1,1,3,3-pentafluorobutane, to flow through the apparatus. In the case of conducting the third to fifth processes by a continuous operation, it is possible to conduct the sixth process without necessity of taking the deteriorated catalyst out.

The regeneration temperature is preferably from a first temperature that is lower than the reaction temperature of the first to fifth processes by 100° C. to a second temperature that is higher than that by 200° C. In terms of operability, it is easy to conduct the regeneration at a temperature in the vicinity of the reaction temperature. If desired, it is possible to dilute the halogenated hydrogen gas or halogen gas with an inert gas (e.g., nitrogen). If desired, it is possible to simultaneously conduct the reaction and the catalyst regeneration. For this purpose, it is possible to simultaneously introduce 1,1,1,3,3-pentafluorobutane and a small amount of the halogenated hydrogen gas or halogen gas into the reaction tube. However, for example, in the case of introducing hydrofluoric acid as the catalyst regeneration gas, too much amount of hydrofluoric acid may adversely affect the reaction. Although the treatment time for regenerating the catalyst depends on the degree of deterioration of the catalyst, it may be about 24 hr. In case that the regeneration effect has not been sufficient by this 24 hr treatment, it is possible to conduct another treatment for about 24 hr at a temperature that is higher than the prior treatment by about 50° C. In case that the regeneration effect has not been sufficient even by repeating such treatment, it is recommended to replace the used catalyst with new one. In the following, the present invention is illustrated in detail by examples. The present invention is not limited to these examples.

EXAMPLE 1

A nickel reaction tube of ¾ inches (1.905 cm) diameter and 36 inches (91.4 cm) total length (filled with 200 ml of nickel Propack (void ratio=96%) of 0.24 inches (0.61 cm)) was heated at temperatures shown in 1-1 to 1-4 of the following Table 1. Under these conditions, 1,1,1,3,3-pentafluorobutane was vaporized by a vaporizer and was allowed to flow at a rate of 70 g/hr. The outflow gas, which had passed through the reaction tube, was passed through water in order to remove hydrogen fluoride (HF). Then, it was dried with calcium sulfate and collected, followed by analysis by gas chromatography (FID, hereinafter the same).

The inside volume of the reaction tube in the present example is 261 cm$^3$, and the volume ("column volume") except the solid phase section of the filler is 253 cm$^3$. The raw material input standard contact time is from 29 seconds (1-4) to 32 seconds (1-1).

The results were shown in Table 1. "GC %" refers to areal % of each component of the above reaction mixture measured by FID.

TABLE 1

| No. | Temp. ° C. | 365 mfc GC % | $CF_3CH_2CF=CH_2$ GC % | (E)-$CF_3CH=CFCH_3$ GC % | (Z)-$CF_3CH=CFCH_3$ GC % |
|---|---|---|---|---|---|
| 1-1 | 450 | 73.7 | 18.6 | 3.8 | 2.7 |
| 1-2 | 470 | 69.5 | 23.4 | 4.3 | 2.8 |
| 1-3 | 500 | 63.5 | 29.6 | 4.3 | 1.3 |
| 1-4 | 520 | 36.4 | 56.9 | 3.4 | 1.6 |

The products were identified by mass spectrometry and NMR (1H, 19F and 13C) and isolated with a purity of 97% by distillation (boiling point: 29-30° C.) under normal pressure. The data are written in the following.

$$CF_3CH_2CF=CH_2 \quad (1)$$

a colorless, transparent liquid $^1$H-NMR solvent: CDCl$_3$, standard substance: TMS δ: 4.88 (dd, J=16.2 Hz, 3.5 Hz, 1H), 4.59 (dd, J=47.3 Hz, 3.5 Hz, 1H), 3.01(dq, J=16.7 Hz, 9.9 Hz, 2H)

$^{19}$F-NMR solvent: CDCl$_3$, standard substance: CFCl$_3$ δ: −66.2 (s, 3F), −95.5~−96.5 (m, 1F)

$^{13}$C-NMR solvent: CDCl$_3$, standard substance: TMS δ: 156.54 (d, J=254 Hz), 124.54 (q, J=277 Hz), 96.40(d, J=18.0 Hz), 37.63(dq, J=32 Hz, 30 Hz) GLC-MS m/z (rel. intensity), 128(M$^+$, 75.2), 113(5.6), 109(9.2), 95(7.6), 89(23.2), 77(9.6), 75(3.2), 69(22.8), 64(100), 59(68.8), 51(13.6), 45(16.4)

$$(E)\text{-}CF_3CH=CFCH_3 \quad (2)$$

a colorless, transparent liquid $^1$H-NMR solvent: CDCl$_3$, standard substance: TMS δ: 5.44 (dq, J=16.9 Hz, 7.6 Hz, 1H), 2.14 (d, J=18.7 Hz, 3H)

$^{19}$F-NMR solvent: CDCl$_3$, standard substance: CFCl$_3$ δ: −57.2 (s, 3F), −79.5 (s, 1F) GLC-MS m/z (rel. intensity), 128(M$^+$, 44.0), 113(70.4), 109(32.0), 89(29.2), 78(12.8), 77(23.6), 69(22.4), 64(22.8), 59(29.6), 57(24.4), 51(18.8), 45(14.8), 39(100)

(Z)-CF$_3$CH=CFCH$_3$   (3)

a colorless, transparent liquid $^1$H-NMR solvent: CDCl$_3$, standard substance: TMS δ: 5.00 (dq, J=32.7 Hz, 7.6 Hz, 1H), 1.99 (d, J=18.7 Hz, 3H)

$^{19}$F-NMR solvent: CDCl$_3$, standard substance: CFCl$_3$ δ: −58.9 (dd, J=17.1 Hz, 6.4 Hz, 3F), −83.2~−83.7 (m, 1F) GLC-MS m/z rel. intensity), 128(M$^+$, 44.0), 113(72.0), 109(37.2), 89(31.2), 78(11.6),

77(25.6), 69(25.6), 64(22.4), 59(29.6), 57(25.2), 51(20.0), 45(15.2), 39(100)

EXAMPLE 2

A (polytetrafluoroethylene) coating magnetic stirring bar, a dropping funnel (under the liquid level), and a Vigreux column were attached to a 250 ml flask. The outlet of the column was passed into an oil bubbler, and it was connected to a collector cooled down to −78° C. 80 g of 85% potassium hydroxide (in the form of flakes) were added to the flask, and it was heated to 210° C. using an oil bath, followed by gradual dropping of 1,1,1,3,3-pentafluorobutane. The products and the unreacted raw material were collected by the collector. The obtained mixture contained seven kinds of products in addition to the raw material. In gas chromatograph area at the reaction termination, the raw material was in 50%, (E-) configuration was in 17.8%, (Z-) configuration was in 17.8%, CF$_3$CH$_2$CF=CH$_2$ was in 8.0%, and the remainder of 6.4% was a mixture containing butadiene and butyne. It was possible to easily separate (E)-CF$_3$CH=CFCH$_3$ (boiling point: 18-19° C.) and (Z)—CF$_3$CH=CFCH$_3$ (boiling point: 48-49° C.) with a purity of 98% or higher by distillation. These structures were identified by mass spectroscopy and NMR.

EXAMPLES 3-1 TO 3-4

In each of Examples 3-1 to 3-4, a catalyst pretreatment was conducted as follows. 15 g of a catalyst obtained by the after-mentioned Catalyst Preparation Example 1 were put into a center portion of a stainless steel reaction tube (inner diameter: 28.4 mm; axial length: 400 mm). While nitrogen gas was allowed to flow at a rate of 50 ml/min through the reaction tube, the temperature was gradually raised to 500° C. After holding this condition for 5 hr, the heating was terminated, followed by cooling to 50° C. After that, hydrochloric acid (hydrogen chloride gas) was introduced into the reaction tube in a manner that the flow rate of HCl was initially 5 ml/min and then gradually raised to 50 ml/min, while the flow rate of nitrogen gas was lowered from 50 ml/min to 10 ml/min. Then, the temperature was raised at a rate of 100° C./hr to 400° C. This condition was maintained for 3 hr, thereby completing the catalyst pretreatment.

Then, 1,1,1,3,3-pentafluorobutane (365mfc), vaporized by a vaporizer, was introduced into the reaction tube at a reaction temperature shown in Table 2 and at a rate to have a raw material input standard contact time shown in Table 2, while nitrogen gas was also introduced at a rate of 10 ml/min. The flow of nitrogen gas was, however, neglected in the calculation of the raw material input standard contact time. The outflow gas, which had passed through the reaction tube, was passed through water in order to remove hydrogen fluoride (HF). Then, it was dried with calcium sulfate and collected, followed by analysis by gas chromatography (FID, hereinafter the same). The results are shown in Table 2.

EXAMPLES 4-1 TO 4-4

Examples 3-1 to 3-4 were repeated except in that the catalyst obtained by the after-mentioned Catalyst Preparation Example 2 was used and that reaction conditions were modified as shown in Table 2. The results are also shown in Table 2. 1,1,3-trifluorobutadiene (purity: 95%) was isolated from the product of Example 4-4 by a distillation under normal pressure and at a distillation tower temperature of 16° C.

EXAMPLES 5-1 TO 5-2

Examples 3-1 to 3-4 were repeated except in that the catalyst obtained by the after-mentioned Catalyst Preparation Example 3 was used and that reaction conditions were modified as shown in Table 2. The results are also shown in Table 2.

TABLE 2

| Catalyst | Reaction Temp (°C.) | RMISCT* (s) | 365 mfc GC % | CF$_3$CH$_2$CF=CH$_2$ GC % | (E)-CF$_3$CH=CFCH$_3$ GC % | (Z)-CF$_3$CH=CFCH$_3$ GC % | CF$_2$=C=CH$_2$ GC % | CF$_2$=CH—CF=CH$_2$ GC % |
|---|---|---|---|---|---|---|---|---|
| Ex. 3-1 | C* | 300 | 30 | 87.3 | 6.8 | 2.2 | 3.7 | 0.0 | 0.0 |
| Ex. 3-2 | C* | 350 | 28 | 48.1 | 29.3 | 10.9 | 9.2 | 0.0 | 2.1 |
| Ex. 3-3 | C* | 400 | 26 | 47.3 | 30.5 | 10.4 | 9.3 | 0.0 | 2.3 |
| Ex. 3-4 | C* | 450 | 24 | 19.5 | 51.8 | 6.5 | 6.1 | 8.9 | 7.3 |
| Ex. 4-1 | Cr/C | 150 | 20 | 91.1 | 4.1 | 1.9 | 3.0 | 0.0 | 0.0 |
| Ex. 4-2 | Cr/C | 200 | 18 | 54.9 | 21.9 | 14.0 | 9.0 | 0.0 | 0.0 |
| Ex. 4-3 | Cr/C | 250 | 16 | 6.3 | 47.1 | 27.9 | 16.0 | 0.0 | 2.5 |
| Ex. | Cr/C | 320 | 14 | 9.8 | 46.2 | 20.4 | 12.3 | 0.0 | 10.5 |

TABLE 2-continued

| Catalyst | Reaction Temp (° C.) | RMISCT* (s) | 365 mfc GC % | $CF_3CH_2CF=CH_2$ GC % | (E)-$CF_3CH=CFCH_3$ GC % | (Z)-$CF_3CH=CFCH_3$ GC % | $CF_2=C=CH_2$ GC % | $CF_2=CH-CF=CH_2$ GC % |
|---|---|---|---|---|---|---|---|---|
| 4-4 | | | | | | | | |
| Ex. 5-1 | Ti/C | 210 | 41 | 58.8 | 32.5 | 2.0 | 1.2 | 0.0 | 0.1 |
| Ex. 5-2 | Ti/C | 250 | 38 | 24.2 | 55.3 | 8.3 | 4.8 | 0.0 | 0.4 |

*C: Activated Carbon
*RMISCT: Raw Material Input Standard Contact Time

EXAMPLES 6-1 TO 6-4

As will be described hereinafter, Examples 6-1 to 6-4 were conducted sequentially. At first, the catalyst pretreatment of Examples 3-1 to 3-4 was repeated except in that 15 g of a catalyst obtained by the after-mentioned Catalyst Preparation 2 were used. Then, the reaction was started by introducing 1,1,1,3,3-pentafluorobutane into the reaction tube at a reaction temperature of 250° C. under a condition to have a raw material input standard contact time of 21 seconds. During the reaction, nitrogen gas was also introduced at a rate of 10 ml/min. The flow of nitrogen was not considered in calculating the raw material input standard time. In Example 6-1, the outflow gas at the initial stage of the reaction was analyzed by gas chromatography. In fact, in Examples 6-1 to 6-4, the outflow gas was treated in the same manner as that of Examples 3-1 to 3-4, prior to the gas chromatography. The reaction was continued for 150 hr under the same conditions as above. In Example 6-2, the outflow gas (150 hr after the start of the reaction) was analyzed by gas chromatography. Since conversion was lowered from 72% (at the initial stage of the reaction) to 48% (150 hr after the start of the reaction), a catalyst regeneration was conducted, as follows. At first, the nitrogen gas flow rate was raised to 50 ml/min, and the introduction of 1,1,1,3,3-pentafluorobutane was stopped. Then, hydrogen chloride was introduced at a rate of 50 ml/min, and the nitrogen gas flow rate was lowered to 10 ml/min. This condition was maintained for 24 hr to regenerate the catalyst, while the temperature of the catalyst layer was maintained at 250° C. After the regeneration, the introduction of hydrogen chloride was stopped. Then, the reaction was restarted under the same conditions as those at the start of the reaction. In Example 6-3, the outflow gas obtained immediately after the catalyst regeneration was analyzed by gas chromatography. After the restart of the reaction, the reaction was continued for 150 hr under the same conditions as above. In Example 6-4, the outflow gas (150 hr after the restart of the reaction) was analyzed by gas chromatography. The results of Examples 6-1 to 6-4 are shown in Table 3.

TABLE 3

| | 365 mfc GC % | $CF_3CH_2CF=CH_2$ GC % | (E)-$CF_3CH=CFCH_3$ GC % | (Z)-$CF_3CH=CFCH_3$ GC % | $CF_2=C=CH_2$ GC % | $CF_2=CH-CF=CH_2$ GC % |
|---|---|---|---|---|---|---|
| Ex. 6-1 (immediately after reaction start) | 28.0 | 32.6 | 25.6 | 13.3 | 0.0 | 0.4 |
| Ex. 6-2 (150 hr after reaction start) | 51.7 | 22.2 | 14.4 | 11.4 | 0.0 | 0.3 |
| Ex. 6-3 (immediately after reaction restart) | 24.0 | 33.1 | 27.6 | 11.6 | 0.0 | 0.7 |
| Ex. 6-4 (150 hr after reaction restart) | 31.0 | 29.1 | 25.0 | 14.3 | 0.0 | 0.5 |

CATALYST PREPARATION EXAMPLE 1

500 g of activated carbon (made by Sigma-Aldrich Corporation) were dried for 24 hr in an vacuum oven at 120° C. under 10 Torr (1,330 Pa). Then, the pressure was increased to atmospheric pressure using nitrogen gas, and the temperature was cooled down to room temperature, thereby completing the preparation of an activated carbon catalyst. The obtained catalyst was put into a sealable glass container, followed by storing the container in a desiccator until its use.

CATALYST PREPARATION EXAMPLE 2

45.8 g of $Cr(NO_3)_3$ were dissolved in 400 g of ion-exchanged water. The resulting solution was gradually added to 100 g of activated carbon (made by Sigma-Aldrich Corporation). Stirring was conducted slowly immediately after the addition and 1 hr after that, followed by standing still for 48 hr. Then, water was removed by a rotatory evaporator, followed by drying for 24 hr in a vacuum oven at 150° C. under 10 Torr (1,330 Pa), thereby preparing a Cr/C catalyst. This catalyst was put into a sealable container, followed by storing the container in a desiccator until its use.

CATALYST PREPARATION EXAMPLE 3

100 g of the activated carbon (obtained in Catalyst Preparation Example 1) were put onto a recrystallization dish. Then, 59.2 g of titanium(IV) isopropoxide [Ti(OCHMe$_2$)$_4$] (made by Sigma-Aldrich Corporation) were slowly added with stirring, followed by standing still for 48 hr. Then, 100 g of ion-exchanged water were sprayed using a spray gun, followed by drying for 48 hr in a vacuum oven at 150° C.

under 10 Torr (1,330 Pa), thereby preparing a Ti/C catalyst. This catalyst was put into a sealable container, followed by storing the container in a desiccator until its use.

COMPARATIVE EXAMPLE 1

A nickel reaction tube of ¾ inches (1.91 cm) diameter and 36 inches (91.4 cm) total length was heated to 630° C., and the reaction tube was filled with a nickel Pro-pack (void ratio=96%) of 0.24 inches (0.61 cm) for the purpose of obtaining higher mixing effect and heat transfer effect. In this condition, 1,1,1,4,4,4-hexafluorobutane was gasified by the same process as that of Example 1 and introduced at a flow rate such that the raw material input standard contact time became 30 seconds. The gas, which had passed the tube, was passed through water in order to remove hydrogen fluoride (HF), followed by drying with calcium sulfate and then gas chromatograph analysis.

As a result, the gas chromatograph area of the raw material 1,1,1,4,4,4-hexafluorobutane was 43.2%, and 30.6% 3,3,3-trifluoropropene and 17.1% trifluoromethane were additionally detected. The target 1,1,4,4,4-pentafluoro-1-butene was not detected.

COMPARATIVE EXAMPLE 2

Using the same apparatus as that of Comparative Example 1, 2-(trifluoromethyl)-1,1,1-trifluoropropane was introduced in the form of gas at 660° C. As a result of conducting the GC analysis of the outflow gas, the raw material was in 18.9%, 3,3,3-trifluoropropene was in 24.5%, and trifluoromethane was in 43.5%. The target 2-trifluoromethyl-1,1-difluoropropene was not detected.

The invention claimed is:

1. A process for producing (E)- and (Z)-1,1,1,3-tetrafluoro-2-butenes, characterized in that 1,1,1,3,3-pentafluorobutane is heated at from about 200° C. to about 700° C.

2. A process for producing (E)- and (Z)-1,1,1,3-tetrafluoro-2-butenes, characterized in that 1,1,1,3,3-pentafluorobutane is brought into contact with a base.

3. A process for producing (E)- and (Z)-1,1,1,3-tetrafluoro-2-butenes according to claim 2, characterized in that the contact of the 1,1,1,3,3-pentafluorobutane with the base is conducted at from 0° C. to 300° C.

4. A process for producing (E)- and (Z)-1,1,1,3-tetrafluoro-2-butenes according to claim 2, characterized in that the base is a base selected from alkali metal hydroxides, alkali earth metal hydroxides, and tertiary amines.

5. A process for producing (E)- and (Z)-1,1,1,3-tetrafluoro-2-butenes according to claim 3, characterized in that the base is a base selected from alkali metal hydroxides, alkali earth metal hydroxides, and tertiary amines.

6. A process for producing (E)- and (Z)-1,1,1,3-tetrafluoro-2-butenes according to claim 2 characterized in that the contact of the 1,1,1,3,3-pentafluorobutane with the base in claim 2 is conducted under a coexistence with water, an ether, a halogen solvent, or a phase transfer catalyst.

7. A process for producing and isolating (E)-1,1,1,3-tetrafluoro-2-butene, characterized in that a reaction mixture containing (E)- and (Z)-1,1,1,3-tetrafluoro-2-butenes is obtained by the contact with the base in claim 2, and then the mixture is subjected to a distillation.

8. A process for producing and isolating (Z)-1,1,1,3-tetrafluoro-2-butene, characterized in that a reaction mixture containing (E)- and (Z)- 1,1,1,3-tetrafluoro-2-butenes is obtained by the contact with the base in claim 2, and then the mixture is subjected to a distillation.

9. A process for producing (E)- or (Z)-1,1,1,3-tetrafluoro-2-butene, comprising heating 1,1,1,3,3-pentafluorobutane in the presence of a catalyst that is selected from the group consisting of (a) an active metal species, (b) a material that is known as a catalyst carrier and has a large specific surface area, and (c) a carried catalyst in which an active metal species is carried on a catalyst carrier.

10. A process according to claim 9, wherein the catalyst is an activated carbon.

11. A process according to claim 9, wherein the catalyst is the carried catalyst in which an active metal species selected from the group consisting of titanium, chromium, manganese, iron, cobalt, nickel, zirconium, niobium, molybdenum, tantalum, and tungsten is carried on an activated carbon.

12. A process according to claim 11, wherein the activated metal species is chromium or titanium.

13. A process according to claim 12, wherein the heating is conducted at a temperature of from 200° C. to 300° C.

14. A process according to claim 9, further comprising distilling a reaction product of the heating, thereby isolating (E)- or (Z)-1,1,1,3- tetrafluoro-2-butene.

15. A process according to claim 9, further comprising regenerating the catalyst by bringing a hydrogen halide gas or halogen gas into contact with the catalyst.

16. A process for producing (E)- or (Z)-1,1,1,3-tetrafluoro-2-butene, comprising subjecting 1,1,1,3, 3-pentafluorobutane to a gas-phase catalytic dehydrofluorination.

* * * * *